US00PP23339P3

(12) United States Plant Patent
Leis et al.

(10) Patent No.: US PP23,339 P3
(45) Date of Patent: Jan. 22, 2013

(54) STRAWBERRY PLANT NAMED 'CAPRI'

(50) Latin Name: ***Fragaria×ananassa* Duch.**
Varietal Denomination: CAPRI

(75) Inventors: Michelangelo Leis, Ferrara (IT); Alessio Martinelli, Ferrara (IT); Gianfranco Castagnoli, Quingentole (IT); Donata Azzolini, legal representative, Quingentole (IT); Pietro Castagnoli, legal representative, Quingentole (IT); Alessandro Castagnoli, legal representative, Quingentole (IT)

(73) Assignee: C.I.V. —Consorzio Italiano Vivaisti—Societá Consortile A R.L., Ferrara (IT)

( * ) Notice: Subject to any disclaimer, the term of this patent is extended or adjusted under 35 U.S.C. 154(b) by 0 days.

(21) Appl. No.: 13/137,434

(22) Filed: Aug. 15, 2011

(65) Prior Publication Data

US 2012/0210478 P1 Aug. 16, 2012

(30) Foreign Application Priority Data

Feb. 14, 2011 (QZ) ..... PBR 20110360

(51) Int. Cl.
*A01H 5/00* (2006.01)

(52) U.S. Cl. ..... Plt./209

(58) Field of Classification Search ..... Plt./209
See application file for complete search history.

*Primary Examiner* — Annette Para
(74) *Attorney, Agent, or Firm* — Foley & Lardner LLP

(57) ABSTRACT

A new and distinct variety of *Fragaria×ananassa* Duch. named 'CAPRI', characterized by the description herein.

4 Drawing Sheets

Latin name of the genus and species claimed: *Fragaria× ananassa* Duch.

Variety denomination: 'CAPRI'.

BACKGROUND OF THE INVENTION

The present invention relates to a new and distinct strawberry variety named 'CAPRI', which was the result of a controlled cross between the strawberry variety 'CIVRI-30' (Registered, CPVO Grant No. 14561) and a not released selection of Consorzio Italiano Vivaisti named R6R1-26.

The progeny was first asexually propagated by stolons in S. Giuseppe di Comacchio Ferrara, Italy, in 2005.

The 'CAPRI' variety was tested over the next several years in different European areas with continental climates. The tests ran from 2006 to 2010.

BRIEF SUMMARY OF THE INVENTION

Plants of the new Strawberry variety 'CAPRI' can be distinguished from plants of the Strawberry variety 'CIVRI-30' by the following unique combination of characteristics described in Table 1:

TABLE 1

| Comparison with Comparison Variety | | | |
|---|---|---|---|
| Denomination of similar variety | Characteristic in which the similar variety is different | State of expression of similar variety | State of expression of candidate variety |
| CIVRI-30 | Fruit Size<br>Plant Vigor<br>Plant habit | Medium to Large<br>Weak to Medium<br>Flat globose | Large<br>Medium to Strong<br>Semi-upright |

Asexual reproduction of this new variety by stolons shows that the foregoing and all other characteristics and distinctions come true to form and are established and transmitted through succeeding propagations. The new variety reproduces true to type.

BRIEF DESCRIPTION OF THE PHOTOGRAPHS

The accompanying photographs illustrate the overall appearance of the new Strawberry 'CAPRI' showing the colors as true as is reasonably possible with colored reproductions of this type. Colors in the photographs may differ slightly from the color value cited in the detailed botanical description, which accurately describe the color of 'CAPRI'.

Figure 1:
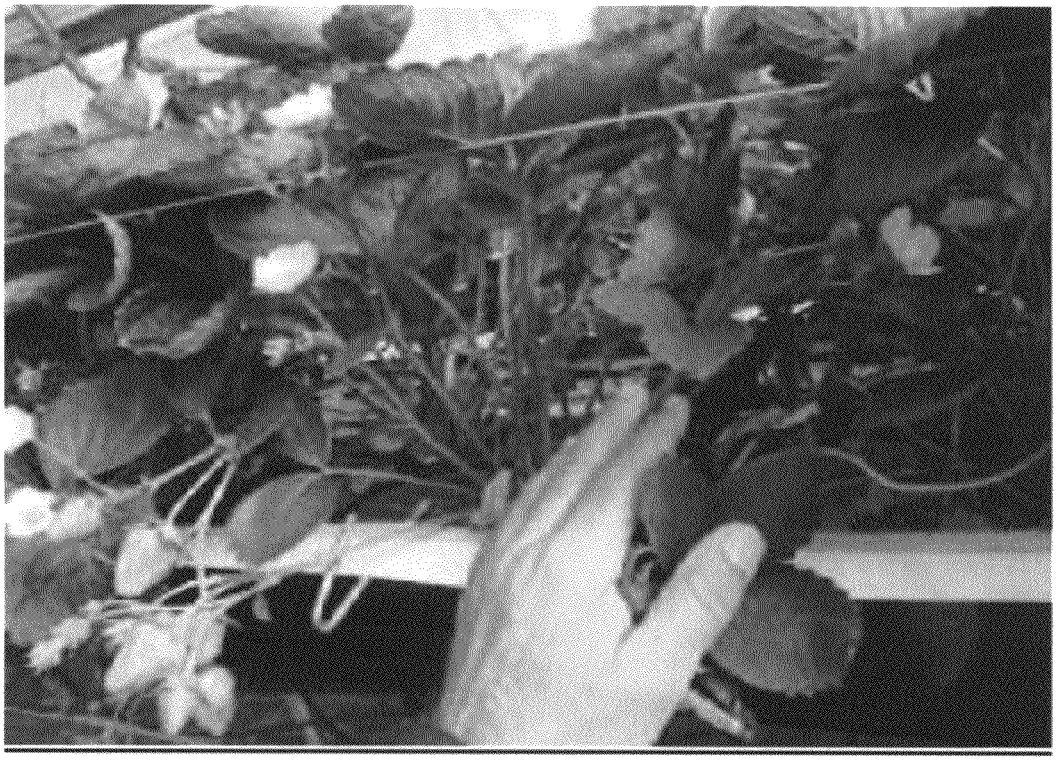
FIG. 1 shows the plant of 'CAPRI'.
Figure 2:
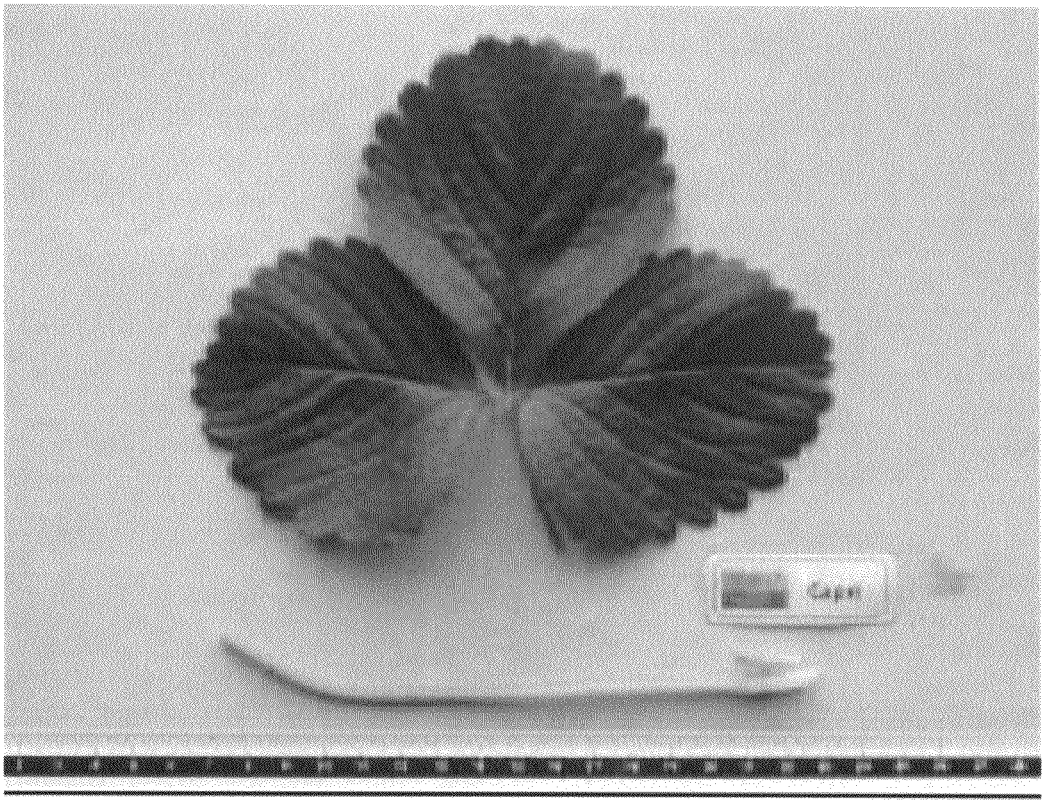
FIG. 2 shows the leaves of 'CAPRI'.
Figure 3:
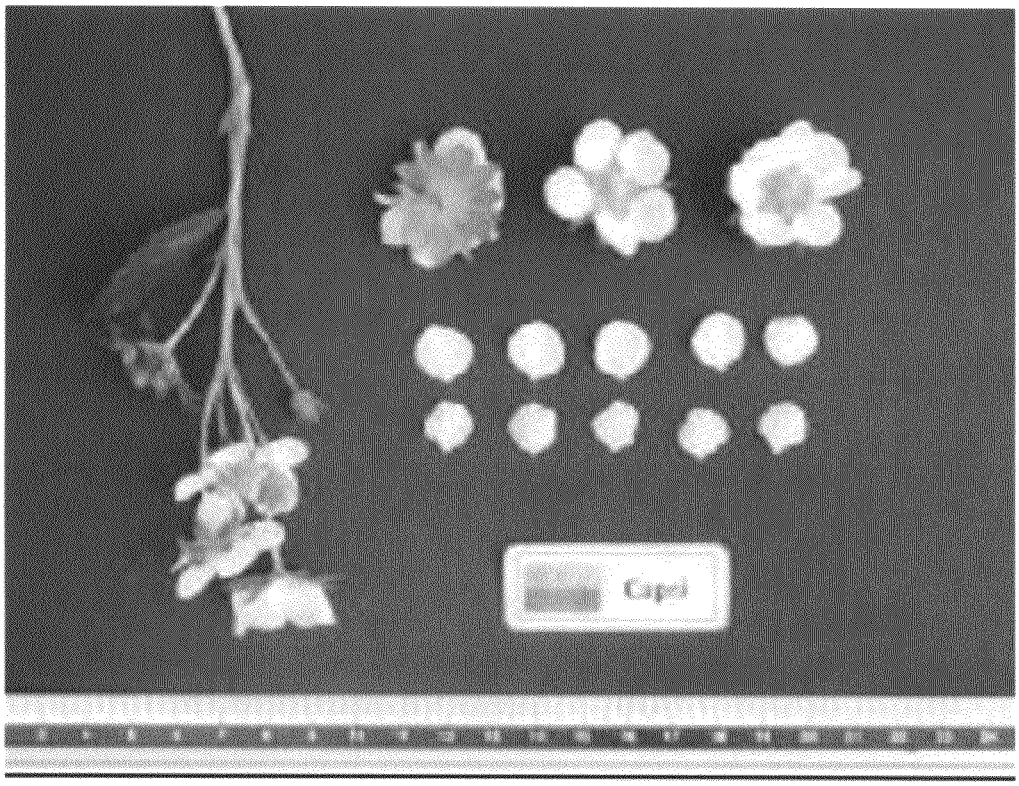
FIG. 3 shows the flowers of 'CAPRI'.
Figure 4:
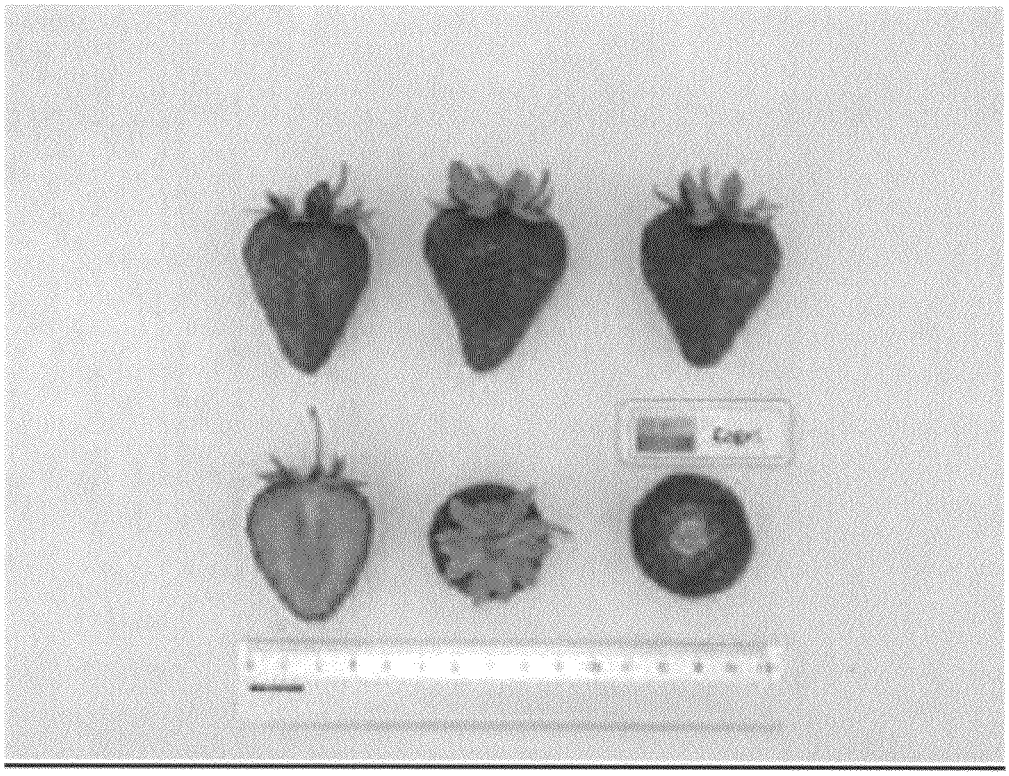
FIG. 4 shows the fruits of 'CAPRI'.

The colors of this illustration may vary with lighting conditions and, therefore, color characteristics of this new variety should be determined with reference to the observations described herein, rather than from these illustrations alone.

DETAILED BOTANICAL DESCRIPTION

The following detailed description of the 'CAPRI' variety, unless otherwise noted, is based on observations taken of plants and fruits, and asexually reproduced progeny, grown at S. Giuseppe di Comacchio, Ferrara, Italy.

The observed plants were one year old plants, produced in a nursery in S. Giuseppe di Comacchio, Italy, then planted as cold stored plants in April.

Certain characteristics of this variety may change with changing environmental conditions (e.g., light, temperature, moisture, etc.), nutrient availability, or other factors. Quantified measurements are expressed as an average of measurements taken from a number of individual plants of the new variety. The measurements of any individual plant, or any group of plants, of the new variety may vary from the stated average. Color descriptions and other terminology are used in accordance with their ordinary dictionary descriptions, unless the context clearly indicates otherwise. Color designations are made with reference to The Royal Horticultural Society (R.H.S.) Colour Chart.

Plant:

*Habit.*—Semi-upright.
*Density.*—Medium.
*Vigor.*—Medium to Strong.
*Overall shape.*—Slightly Upright.
*Height.*—0.30 meters.
*Width.*—0.35 meters.

Leaf:

*Upperside.*—RHS 137A green group; underside: RHS 138B green group.
*Length.*—0.10 meters.
*Width.*—0.09 meters.
*Cross section.*—Concave.
*Leaf surface undulation or blistering.*—Absent to very weak.
*Number of leaflets.*—Three only.
*Leaf stem characteristics.*—Color RHS 145A yellow-green group. Position of hairs: upwards. Length: About 19 cm.
*Terminal leaflet.*—Length/width ratio: moderately longer. Length: About 10 cm. Width: About 9 cm. Shape of base: Obtuse. Shape of teeth: Crenate.
*Petiole.*—Position of hairs: Upwards. Length: About 19 cm.
*Stipule.*—Color RHS 144D yellow-green group; Anthocyanin coloration: weak; Color RHS 45C red group.
*Stolons.*—Number about 7-9. Thickness: Medium, about 2.9 mm. Pubescence: Medium. Color RHS 144C, yellow green with medium presence of anthocyanin coloration, RHS 46A red.

Inflorescence: Position relative to foliage: at same level. Length: About 25 cm.

*Flower.*—Size: Medium. Size of calyx relative to corolla: Same size. Spacing of petals. Overlapping.
*Flower characteristics.*—Diameter primary flowers. About 3 cm. Diameter secondary flowers. About 2.5 cm. Number of petals: about 5 to 7. Fragrance: No significant fragrance. Time from bloom to mature fruit: About 30 to 35 days.

Reproductive organs:

*Stamens.*—Numerous with pollen present, fertile and abundant. Length: approximately 3 mm. Color: RHS 157A, green-white.
*Anthers.*—Generally average in size, about 1.2 mm by 0.7 mm. Color: RHS 14B yellow orange; darkening with advanced maturity.
*Pollen.*—Fertile and abundant. Color: RHS 17B yellow orange.
*Pistils.*—Numerous, generally average in size. Color: RHS 151D yellow green.
*Petal.*—Length/width ratio: equal.

Fruit:

*Fruit truss.*—Attitude: Semi-erect.
*Ratio of length/maximum width.*—Moderately longer than broad.
*Color of mature fruit.*—RHS 46A, red.
*Color of internal fruit.*—RHS 33A orange-red, RHS 35A orange-red, and RHS 155D white.
*Length.*—45-50 mm.
*Width.*—40-45 mm.
*Calyx diameter.*—40-45 mm.
*Average weight.*—20-33 grams.
*Achene color.*—RHS 153C yellow green.
*Number of achenes per berry.*—About 510-580.
*Achene size.*—Length about 1.2 mm, width about 0.7 mm.
*Weight of* 1000 *achenes.*—0.40 grams.
*Peduncle length of inflorescence stem.*—Primary fruit about 9-11 cm, secondary fruit about 6-7 cm, color RHS 139D, green.
*Marketable yield* (*gm/plant*).—About 1.000 to 1.200 grams.
*Fruit size.*—Large.
*Predominant shape.*—Conical.
*Difference in shapes between primary and secondary fruit.*—Moderate.
*Band without achenes.*—Absent to very narrow.
*Unevenness of surface.*—Even to very slightly uneven.
*Evenness of color.*—Even to very slightly uneven.
*Glossiness.*—Strong.
*Insertion of achenes.*—Level with surface.
*Insertion of calyx.*—Level with fruit.
*Attitude of the calyx.*—Outwards.
*Size of calyx in relation to fruit diameter.*—Same size.
*Adherence of calyx.*—Medium.
*Firmness of flesh.*—Firm.
*Hollow center expression.*—Absent or small.
*Flavor.*—Very good.
*Soluble solids* (% *brix*).—About 7.5 to 8.5.
*Time of first flowering.*—About 30-35 days after planting of fresh plants.
*Time of first harvesting.*—About 30-35 days after first flowering.
*Harvest period.*—June to November.
*Type of bearing.*—Fully remontant.

Disease resistance: The 'CAPRI' variety has been tested for several years and it has manifest a good rusticity plant, with medium-dense foliage and excellent resistance to most common fungal diseases, moderately susceptible to leaf spot, and tolerant to mildew.

What is claimed is:

1. A new and distinct variety of *Fragaria×ananassa* Duch. plant named 'CAPRI', as illustrated and described herein.

* * * * *